United States Patent [19]

Tissier et al.

[11] Patent Number: 4,813,781
[45] Date of Patent: Mar. 21, 1989

[54] METHOD OF MEASURING THE FLOWING OF A MATERIAL

[76] Inventors: Annie Tissier, 10, Domaine Plantees, Biviers, 38330 Saint Ismier; Didier Dutartre, 4, Allee du Bret, 38240 Meylan, both of France

[21] Appl. No.: 89,556

[22] Filed: Aug. 26, 1987

[30] Foreign Application Priority Data

Aug. 26, 1986 [FR] France ................. 86 12294

[51] Int. Cl.$^4$ ............................................. G01B 9/02
[52] U.S. Cl. .................................... 356/354; 374/161
[58] Field of Search ............... 356/354, 345, 72, 43, 356/358; 374/161

[56] References Cited

U.S. PATENT DOCUMENTS

| | | |
|---|---|---|
| 3,985,444 | 10/1976 | Takashima et al. |
| 4,140,397 | 2/1979 | Gara . |
| 4,188,123 | 2/1980 | Kleinknecht ................. 356/354 |
| 4,200,396 | 4/1980 | Kleinknecht et al. .......... 356/354 |
| 4,525,066 | 6/1985 | Guillaume et al. ............ 374/161 |

FOREIGN PATENT DOCUMENTS 2537563 3/1987 Fed. Rep. of Germany .
61-108917 10/1986 Japan .

OTHER PUBLICATIONS

K. Dorenwendt et al, "Dimensinal Metrology In Technics by Diffraction of Light", Laserelektrooptic, vol. 19, No. 3 (Sep. 1978): 16, 19.

*Primary Examiner*—Vincent P. McGraw
*Assistant Examiner*—S. A. Turner
*Attorney, Agent, or Firm*—Lowe, Price, LeBlanc, Becker & Shur

[57] ABSTRACT

In a method for measuring the flowing of the material, the following steps: forming an array of parallel strips of said material constituting a diffraction grating; submitting said grating at the same conditions as the material, the flowing of which is to be monitored; illuminating the grating by a single wavelength light beam and observing the diffracted light.

6 Claims, 3 Drawing Sheets

METHOD OF MEASURING THE FLOWING OF A MATERIAL

FIELD OF THE INVENTION

The instant invention relates to a method for directly measuring during the thermal flow of a material the flowing degree of this material.

The instant invention applies in particular to integrated circuits wherein the invention is used for quality controls during manufacturing.

BACKGROUND OF THE INVENTION

When manufacturing integrated circuits, silicon dioxide ($SiO_2$) layers are commonly used, in particular for insulating successive conductive layers from the bulk of the integrated circuits. Those silicon dioxide layers are generally formed from a deposition of silicon dioxide on the whole surface of an integrated circuit wafer, this layer being then etched by various photo-etching methods including a chemical etch or a plasma etch. The edges of the remaining silicon dioxide layer portions after the etching are generally very stiff and form steps. This can cause, when further depositing a metallic layer such as an aluminum layer, a poor overlap of the edges and possibly metal breakings and accordingly an interruption of the conductive circuits. Therefore, one wishes to round the edges of the silica layer portions. This is generally carried out by curing at a temperature higher than the vitrous-transition temperature of the silica for causing its flowing. Very often, for reducing the temperature of this thermal step, a "dopant" such as boron or phosphorous is incorporated into silica.

It is wishable to reduce as much as possible the time duration of the flowing thermal step. This duration has to be long enough for obtaining a wished rounding of the edges and must not be too long. On the one hand, every thermal step during the manufacturing of an integrated circuit has an influence on the steps formerly carried out on the circuit; in particular, it causes a diffusion of the dopants formerly diffused into the semiconductive layers and modifies the configuration of the active areas. On the other hand, an excessive flowing could impair the operation of the circuits for example due to a large reduction of the insulator thickness on some raised portions of the underlying layers.

Here is the problem that the invention aims to solve. Indeed, thin doped silica layers obtained for example by chemical vapor deposition (CVD) are not highly reproducible, as regards their composition, in particular during plasma enhanced deposition. As the glass viscosity is very dependent upon its doping level, small variations in the silica composition from a wafer to another and from a manufacturing batch to another will cause important variations in the flowing speed and accordingly in the obtained configurations.

Thus, presently, for determining the time duration of the flowing step, an X-ray analysis or a chemical analysis of the doping level of a silica layer is carried out, but those analysis give only a general value of the doping level while only the boron or phosphorous solved in the form of B O or P O have an action on the vitrous transition temperature. Therefore, it is not possible to obtain a measuring permitting to derive precise values of the thermal step.

Another method consists in making a test on a reference wafer, carrying out a flowing operation, then cleaving the wafer and observing the shape of the steps through an electronic microscope. Then the thermal step of the actual plate is carried out with the optimal value obtained from the reference wafers. This method presents the drawback of necessiting a reference wafer and carrying out thereon a plurality of operations.

Therefore, an object of the instant invention is to provide for a method permitting to measure in situ the flowing of a layer of a material and a device for implementing this method.

SUMMARY OF THE INVENTION

To attain this object, the instant invention provides for a flowing measuring method of a material comprising the steps consisting in : forming an array of parallel stripes of said material forming a diffraction grating; submitting said grating to the same conditions as the material the flowing of which is to be controlled; illuminating the grating by a single frequency light beam and observing the variation of the diffracted light during the flowing.

More particularly, the instant invention provides for a method wherein said material comprises portions of a silica layer, possibly doped, formed upon an integrated circuit plate being manufactured and wherein said grating is found only on a portion of at least one of a set of simultaneously manufactured plates.

According to embodiment of the invention, the step of observing the diffracted light comprises the steps consisting in measuring the intensity of at least a light spot of the diffracted image and deducing from said measure the deformation of the grating stripes.

In an apparatus for implementing the instant invention, the light source can be a single frequency laser.

BRIEF DESCRIPTION OF THE DRAWINGS

Those objects, features and advantages and others of the instant invention shall be disclosed in more details in the following description of a preferred embodiment in connection with the attached drawings wherein:

FIGS. 2A-3A, 2B-3B, 2C-3C and 2D-3D show shapes of stripes in a diffraction grating and the corresponding diffraction fringes.

DETAILED DESCRIPTION OF THE DRAWINGS

Figure 1:
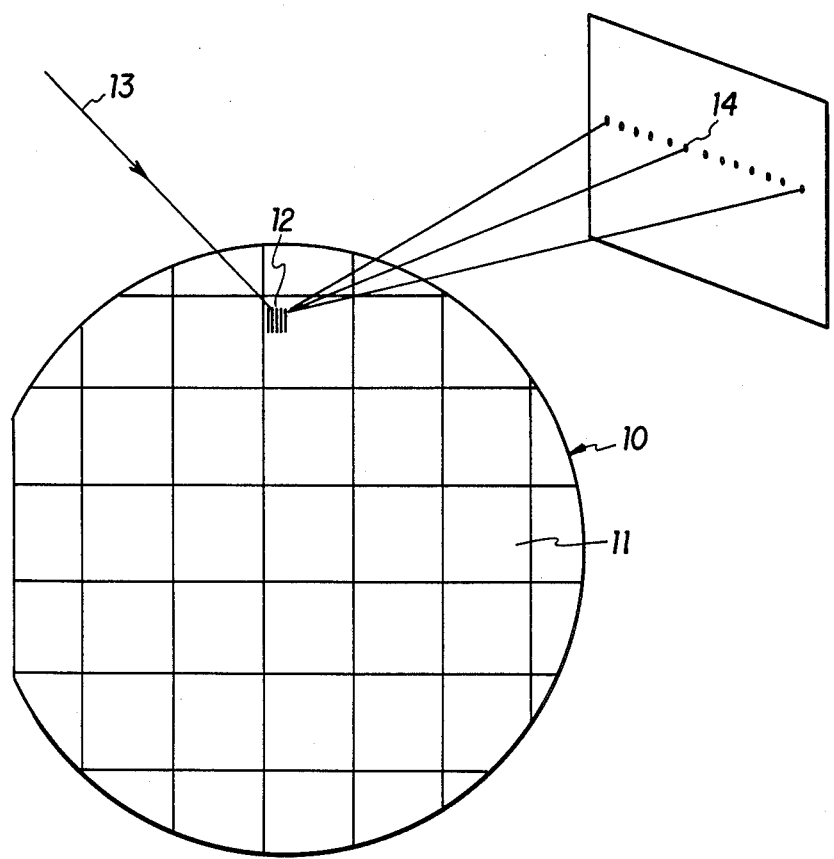
FIG. 1 generally illustrates the method according to the invention.

FIG. 1 very schematically shows a preferred embodiment of the instant invention. On a wafer 10 on/in which a great number of adjacent circuits are manufactured inside blocks 11 (usually squares ou rectangles), during a silica deposition step, one simultaneously deposits silica at a position 12 of the wafer corresponding for example to a non used position during this manufacturing step; and, the silica is etched out at said position according to a parallel stripe pattern having for example substantially the thickness and the width corresponding to the typical thickness and width of the smaller silica stripes that are to be flowed in the active area of the wafer, for example 1 to 5 micrometers. This stripe pattern constitutes an optical diffraction grating. Thus, if the position 12 is illuminated by a light beam 13, one sees on the screen a main light spot 14 corresponding to the specular reflection and a great number of aligned adjacent diffration sposts. Those skilled in the art will easily choose the various parameters of the optical system for determining, for example, the suitable wavelength of the incident beam, the incidence angle and the optical systems to be interposed.

The grating 12 is thus made of the same material as the one that is to be flowed and is deposited onto the same substrate. Thus, the flowing of the stripes of the grating 12 will occur in the same way as the flowing of the active layer stripes, the evolution of which is to be monitored.

FIGS. 2A-2D are crosssection views of a grating stripe used according to the instant invention, the stripes having for example a width of 3 micrometers and being spaced 3 micrometers apart. From FIG. 2A to 2D, the flowing degree increases.

FIGS. 3A-3D show corresponding diffraction fringes, that is intensities of the successive spots. Those intensities can for example be measured through a scanner moving along the diffraction fringes or by sampling through a diode array. It is to be noted that the shape of the diffraction fringes changes relatively regularly while the flowing degree increases.

Figure 2A:
Figure 2B:
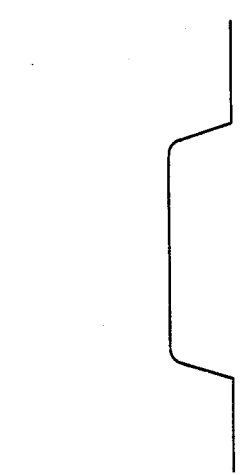
Figure 2C:
Figure 2D:
Figure 3A:
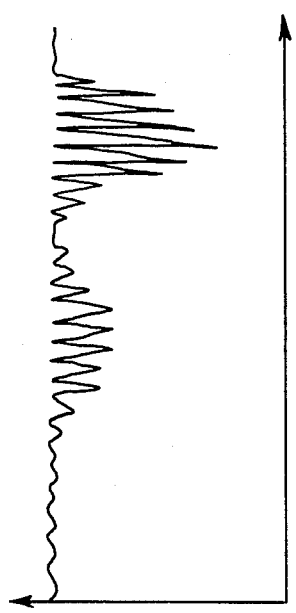
Figure 3B:
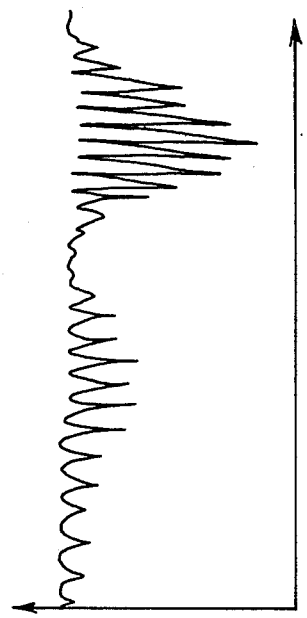
Figure 3C:
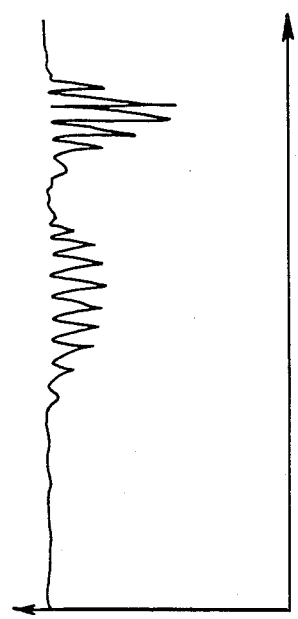
Figure 3D:
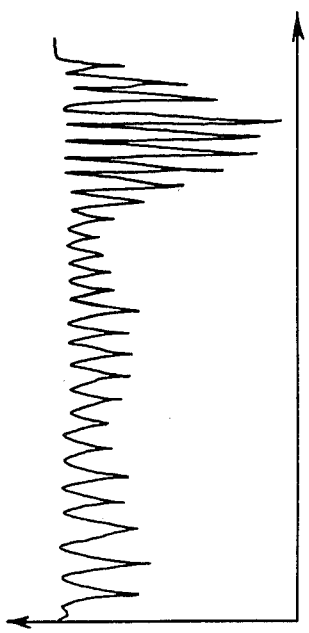

In case of FIGS. 2A and 3A (before flowing) one can see a succession of intense light spots at the neighbourhood of the specular reflection spot and a second series of less intense but relatively intense light spots on both sides of the specular reflection spot (only one side is shown in the drawings). As show in FIGS. 3B-3D, while the flowing level increases, the relative intensity of the more intense spots with respect to the less intense spots decreases and the side spots are more and more intense. Therefore, one obtains a direct correlation between the shape of the stripes constituting the diffraction grating and the obtained diffraction spectrum. Those shapes could be calculated a priori by using classical optical theory. More simply, it will be possible to make a succession of tests and analyze the obtained patterns. Then, it will be for example possible to consider one diffraction spot of a given order and study its variation with respect to a diffraction spot of another order, those two spots being chosen in a particularly characteristic way in the spectrum. A measure of the flowing degree can be directly deduced therefrom. Accordingly, it will be possible to stop the flowing process exactly at the moment where the desired flowing has been obtained.

In an application to integrated circuits, figure 1 shows that a grating pattern made of the material to be flowed is present on one of the chips of a wafer. It can be a useful chip wherein the grating pattern has been introduced in an area not used at least at the considered manufacturing step. It can also be a reference chip disposed at a particular emplacement of the wafer. If the following process is carried out while a wafer batch is treated, the grating pattern can be arranged on each of the wafers, at the condition of being in an easily accessible area of the wafer for having room enough for the incident and diffracted beams. This pattern can also be present on only one active wafer or on a reference wafer treated in the same batch.

Thus, the method according to the invention permits, by analyzing the variation of the diffraction fringes by any means, for example by calculation or by sampling, to optimize the flowing step by getting rid of:

uncontrolled variations of the doped silica composition ;

silica viscosity variations possibly originating from variations in the working atmosphere ;

thermal variations originating either from the curing system, either from the plate (thickness, average reflectivity . . .) in case of flash curing.

Additionnally, the instant invention permits to avoid the use of reference wafers treated before the useful batch. At worst, it will be possible to use a reference wafer treated simultaneously with the useful batch.

In a practical implementation, the present method has been applied onto a silicon wafer having a diameter of 100 mm in accordance with the following successive steps :

CVD deposition of silica doped with 8% phosphorous, photoresist deposit, light flooding through a mask comprising in a given area parallel and regularly spaced stripes, and revelating the photoresist, plasma etching the photoresist, disposing the wafer in a lamp curing oven, arranging a helium/neon laser operating at a wave length of 632.8 nm so that it lights the grating formed in the silica covering the wafer, the laser beam being comprised in a plane defined by a stripe of the grating and a line perpendicular to the wafer, detecting the diffracted spots by observing on a screen arranged orthogonally to the zero order spot (specular reflection), curing at 1170° C.

Alternatively, it will be noted that, in a large number of integrated circuits, parallel and regular stripes of silica exist and are to be flowed. This occurs for example in the regular structures of memories or logical arrays. In this case, it will be possible to use directly the method according to the invention on those useful patterns without carrying out the particular auxilliary pattern as disclosed hereinbefore.

We claim:

1. A method for measuring a flowing of a material subjected to high temperature conditions, comprising the steps of:

forming an array of parallel stripes on said material, said stripes constituting a diffraction grating;

subjecting said grating to the same high temperature conditions as said material, the flowing of which material is to be determined;

illuminating said grating with a single wavelength light source to form a diffraction pattern;

measuring an intensity of a light spot of the diffraction pattern; and in response, determining a deformation of the grating stripes caused by flowing of the material comprising said diffraction grating.

2. The method of measuring a flowing of a material subjected to high temperature conditions, according to claim 1, wherein said material comprises portions of a silica layer formed on a integrated circuit wafer being manufactured and wherein said grating is formed on a portion of at least one of a set of simultaneous treated wafers.

3. The method of measuring a flowing of a material subjected to high temperature conditions, according to claim 2, wherein said ilica layer is doped with an impurity.

4. A device for measuring the flowing of a material, at least one portion of said material comprising regularly spaced stripes constituting a diffraction grating, said device comprising:

illumination means for illuminating said parallel stripes constituting a diffraction grating to produce a diffraction pattern; and detecting means for detecting first and second diffraction fringes of respective predetermined different orders of said diffraction pattern and comparing an intensity of said diffraction fringes to determine a deformation of said spaced stripes constituting said diffraction grating.

5. The device for measuring the flowing of a material according to claim 4, wherein said illumination means comprises a laser.

6. A method for measuring a flowing of a material subjected to high temperature conditions, comprising the steps of:

forming an array of parallel stripes on said material, said strips constituting a diffraction grating;

subjecting said grating to the same high temperature conditions as said material, the flowing of which material is to be determined;

illuminating said grating with a single wavelength light source to form a diffraction pattern including first and second light spots of respective lobes of differing orders, both said lobes spaced apart from a lobe of a specular spot;

detecting an intensity of said first and second light spots of the diffraction pattern;

comparing said intensity of said first and second light spots; and determining from said comparison a deformation of the grating stripes caused by flowing of the material comprising said diffraction grating.

* * * * *